(12) United States Patent
Soni et al.

(10) Patent No.: US 7,189,579 B2
(45) Date of Patent: Mar. 13, 2007

(54) ZERO HEADSPACE EXTRACTOR AND METHOD FOR DETERMINING PARTITIONING AND CONTAMINANT RELEASE RATES OF VOLATILE AND SEMI-VOLATILE COMPOUNDS

(75) Inventors: Bhupendra K. Soni, Westmont, IL (US); Thomas D. Hayes, Schaumburg, IL (US)

(73) Assignee: Gas Technology Institute, Des Plaines, IL (US)

( * ) Notice: Subject to any disclaimer, the term of this patent is extended or adjusted under 35 U.S.C. 154(b) by 752 days.

(21) Appl. No.: 10/080,475

(22) Filed: Feb. 22, 2002

(65) Prior Publication Data

US 2003/0162303 A1    Aug. 28, 2003

(51) Int. Cl.
*G01N 1/18* (2006.01)
*G01N 1/00* (2006.01)
*G01N 1/22* (2006.01)
*G01N 1/10* (2006.01)
*B32B 5/02* (2006.01)

(52) U.S. Cl. .................... 436/178; 436/43; 436/174; 436/181; 436/175; 436/177; 422/83; 422/88; 422/101; 422/50; 422/56; 422/68.1; 422/69; 422/80; 422/81; 73/23.2; 73/1.01; 73/1.02

(58) Field of Classification Search ............... 422/83, 422/88, 101, 50, 56, 58, 68.1, 69, 80, 81; 436/43, 174, 178, 181, 177, 175; 73/1.01, 73/1.02, 23.2

See application file for complete search history.

(56) References Cited

U.S. PATENT DOCUMENTS

| | | | |
|---|---|---|---|
| 4,759,227 A | 7/1988 | Timmons | |
| 4,830,643 A | 5/1989 | Sassa et al. | |
| 5,010,776 A | 4/1991 | Lucero et al. | |
| 5,138,101 A * | 8/1992 | Devon | 568/492 |
| 5,181,428 A | 1/1993 | Chriswell | |
| 5,235,863 A * | 8/1993 | Bailey et al. | 73/863.23 |
| 5,355,736 A | 10/1994 | Skogley | |
| 5,470,535 A * | 11/1995 | Ray et al. | 422/101 |
| 5,578,769 A | 11/1996 | Warrington et al. | |
| 5,679,574 A | 10/1997 | Friedman et al. | |
| 5,756,357 A | 5/1998 | Wright et al. | |
| 5,786,527 A | 7/1998 | Tarte | |
| 5,804,743 A * | 9/1998 | Vroblesky et al. | 73/863.23 |
| 5,862,512 A * | 1/1999 | Voorhees et al. | 702/2 |
| 5,889,217 A | 3/1999 | Rossabi et al. | |
| 5,922,974 A | 7/1999 | Davison et al. | |

(Continued)

*Primary Examiner*—Brian Sines
(74) *Attorney, Agent, or Firm*—Mark E. Fejer

(57) ABSTRACT

A method and device for measuring release rates of contaminants in at least one of a fast release mode and a slow release mode in which a volatile liquid sample is introduced into a sealed transparent reactor vessel having at least one sorbent contained within the transparent reactor vessel and a separator for preventing direct contact between the at least one adsorbent and the at least one volatile liquid sample in the transparent reactor vessel, whereby substantially zero headspace is maintained within the transparent reactor vessel. At least one solvent soluble constituent present in the at least one volatile liquid sample is passed through the separator, resulting in sorption of the at least one solvent soluble constituent by the at least one sorbent. In accordance with one preferred embodiment, the separator is a dialysis bag contained in the transparent reactor vessel into which the resin is placed. The at least one solvent soluble constituent is then removed from the at least one sorbent through the separator.

7 Claims, 7 Drawing Sheets

U.S. PATENT DOCUMENTS

| | | |
|---|---|---|
| 5,928,950 A | 7/1999 | Wright et al. |
| 5,996,423 A * | 12/1999 | Baghel et al. ............ 73/863.23 |
| 6,117,682 A | 9/2000 | Lynn et al. |
| 6,196,074 B1 | 3/2001 | Varhol |
| 6,272,938 B1 * | 8/2001 | Baghel et al. ............ 73/863.23 |
| 6,478,961 B2 * | 11/2002 | Petty et al. .............. 210/502.1 |
| 6,588,255 B2 * | 7/2003 | Pawliszyn .................. 73/64.47 |
| 6,591,702 B2 * | 7/2003 | Hayes et al. ................... 73/866 |

* cited by examiner

ZERO HEADSPACE EXTRACTOR AND METHOD FOR DETERMINING PARTITIONING AND CONTAMINANT RELEASE RATES OF VOLATILE AND SEMI-VOLATILE COMPOUNDS

BACKGROUND OF THE INVENTION

1. Field of the Invention

This invention relates to a method and apparatus for determining release rates of contaminants from soils. More particularly, this invention relates to a method and apparatus that allows the use of sorptive resins for determining the release rates of contaminants from soils while avoiding direct contact between the sorptive resin and the soil/NAPL (nonaqueous phase liquid) complexes. The apparatus is a zero headspace extraction device which, in addition to enabling the determination of release rates of contaminants from soils also provides for easy determination of partitioning constants and the conducting of serial dilution partition tests to determine the rapid release fraction of contaminants in soils and soil/NAPL complexes.

2. Description of Related Art

Contamination of subsurface soil and its environmental impact is the subject of considerable attention and causes much concern with respect to the storage and disposal of materials such as waste with the potential for contamination. When exposed to soil, it is common for such contaminating or hazardous materials to lodge in the interstices or pore space of the soil, or to become part of the soil solutions, generally defined as the interstitial water in the soil together with solutes and dissolved gases. It will be apparent that the presence of such contaminating or hazardous materials may not be visually detectable as a result of which problems associated with the presence of such contaminating or hazardous materials may not manifest themselves until they have reached a critical point. Thus, there is a need for methods and devices for obtaining samples of liquid and gas from subsurface soil in order to subsequently analyze some samples for the possible presence of hazardous materials.

It is well known that a substantial amount of subsurface contamination has been caused by the leakage of tanks storing a variety of liquids. One particular problem is the wide spread use of underground storage tanks for various petroleum products with it being known that many of these tanks leak due to corrosion and/or other reasons.

While there are a number of known methods for testing soil for contamination, many of which involve the physical removal of a soil sample and transporting it to a suitable laboratory for analysis, a common problem associated with many of such known methods is the difficulty in determining the spreading or extension of the contamination efficiently and rapidly. That is, while an absolute test may provide a certain reading with respect to soil contamination, the reading may not necessarily be indicative of the contamination extension insofar as its proximity to the actual source of the contamination. Thus, assuming the example of an hydrocarbon leakage, the relative presence in a sample of the hydrocarbon does not necessarily indicate its proximity to the original source of the hydrocarbon since migration of the hydrocarbon can, and does, occur. A further problem arises in connection with soil remediation. Unless the mobility of the contaminants or hazardous materials is first determined, remediation may result in the removal of more soil than necessary to obtain the required cleanup. Yet a further problem, particularly when evaluating the vapor or gaseous phase of a contaminant, is the inconsistency of results obtained. A concentration of organic vapors in a soil does not necessarily correlate effectively to the hydrocarbon contamination. The vapors can travel in the soil from the site of original contamination and can lead to false positive testing. And, this testing may not give a direct relationship between the concentration of the organic vapor in the soil and the concentration of the hydrocarbon in the area.

It will be apparent to those skilled in the art that there are numerous known devices and methods for collecting and analyzing contaminants, including organic compounds, in ground water and soil samples. Many such methods and devices employ semipermeable or permeable membranes. See, for example, U.S. Pat. No. 5,804,743 to Vroblesky et al. which teaches a method and apparatus for monitoring the concentration of contaminants, including volatile organic compounds, in ground water in which a semipermeable membrane which is permeable to contaminants but impermeable to a reference fluid and which forms an inner chamber, is filled with a reference fluid, such as distilled water, and placed in contact with contaminated ground water, thereby allowing contaminants to diffuse through the semipermeable membrane and into the innerchamber. The semipermeable membrane is then removed from contact with the ground water and a sample withdrawn from the inner chamber for analysis. U.S. Pat. No. 5,235,863 to Bailey et al. teaches an apparatus for soil-gas sampling comprising a passive vapor collector comprising a porous polytetrafluoroethylene tubular container filled with a sorbent enclosed within a container which is resistant to liquid water penetration but permeable to vapor. In this way, the container walls permit diffusion of soil-gas vapors from the soil, inward, to the collector.

Also known as a means for isolating contaminants from soil samples are headspace and purge and trap procedures. Most of the zero headspace work is conducted in accordance with USEPA Method No. 1312, which describes the conventional Synthetic Precipitation Leaching Procedure (SPLP) using a large steel vessel referred to as a zero headspace extractor or ZHE. Such a device is shown in FIG. 1. The known ZHE 10 comprises a sealed steel cylinder 11 having a piston 12 disposed therein. The sealed steel cylinder 11 has a pressurized gas inlet/outlet 13 disposed on the motive fluid side 14 of the piston 12 and a sample inlet/outlet 15 disposed on the sample side 16 of the piston 12. The sealed steel cylinder 11 is sealed at both ends by flanges 17 and 18. As can be seen, the volume of sample 19 in the device can be varied through the use of the piston 12. Ratios of soil to water in the range of about 2:1 to about 1:100 can be achieved. In addition to limitations in application and complexities of usage, it is apparent that the cost of this known device, due in part to the materials used to make the device, is relatively high.

SUMMARY OF THE INVENTION

It is one object of this invention to provide a method and apparatus for determining release rates of contaminants from soils.

It is another object of this invention to provide a method and apparatus for determining release rates of contaminants from soils utilizing sorptive resins.

It is another object of this invention to provide a method and apparatus that allows the use of sorptive resins for determining the release rates of contaminants from soils while avoiding direct contact of the resin with the soil/NAPL complex.

It is yet a further object of this invention to provide a low-cost apparatus for easy determination of partitioning constants.

It is another object of this invention to provide an apparatus for conducting serial partition tests to determine the rapid release fraction of contaminants in soils and soil/NAPL complexes.

These and other objects of this invention are addressed by an apparatus comprising a transparent reactor vessel comprising sealable means for introducing at least one volatile liquid sample into the transparent reactor vessel, at least one adsorbent contained within the transparent reactor vessel, and separation means for preventing direct contact between the at least one adsorbent and any soil/NAPL complex present in the transparent reactor vessel, which separation means permits passage of solvent soluble constituents to be sorbed by the at least one adsorbent. This apparatus is a low cost device for contacting soil with a liquid, for maintaining a gas headspace volume equivalent to virtually zero percent of the total contents of the contact chamber and for employing an sorptive resin for measurement of the contaminant releases from the soil into the liquid phase, e.g. water, of the contact vessel without direct contact of the resin with the soil solids. In accordance with one preferred embodiment of this invention, the separation means is a dialysis bag in which the adsorbent is contained, thereby maintaining separation between the adsorbent and the soil/NAPL residues during testing. Solids, including colloidal materials, are kept outside the bag while water soluble constituents, including contaminants desorbed from the soil/NAPL complexes, pass through the bag to be sorbed onto the adsorbent. Thus, only the water soluble (or solvent soluble) volatile/semivolatile contaminants are permitted to be adsorbed by the adsorbent.

In accordance with the method of this invention, a volatile liquid sample is introduced into a transparent reactor vessel comprising sealable means for introducing the at least one volatile liquid sample into the transparent reactor vessel, at least one adsorbent contained within the transparent reactor vessel, and separation means for preventing direct contact between the at least one adsorbent and the at least one volatile liquid sample in the transparent reactor vessel, whereby substantially zero headspace is maintained within the transparent reactor vessel. At least one solvent soluble constituent present in the at least one volatile liquid sample is passed through the separation means, resulting in adsorption of the at least one solvent soluble constituent by the at least one adsorbent. The at least one solvent soluble constituent is then removed from the at least one adsorbent through the separation means for analysis.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
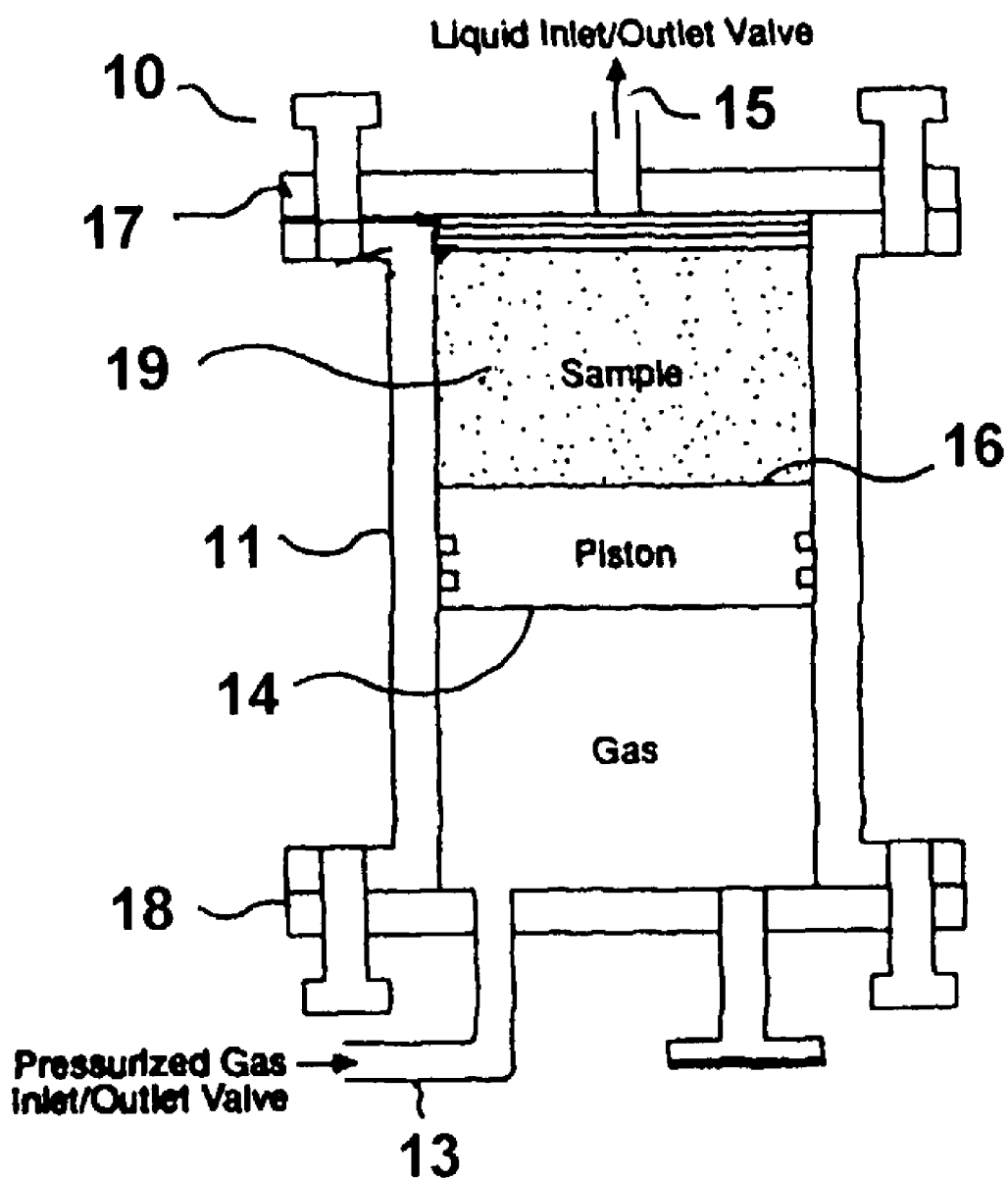
FIG. 1 is a schematic diagram of a known Zero Headspace Extractor (ZHE)
Figure 2:
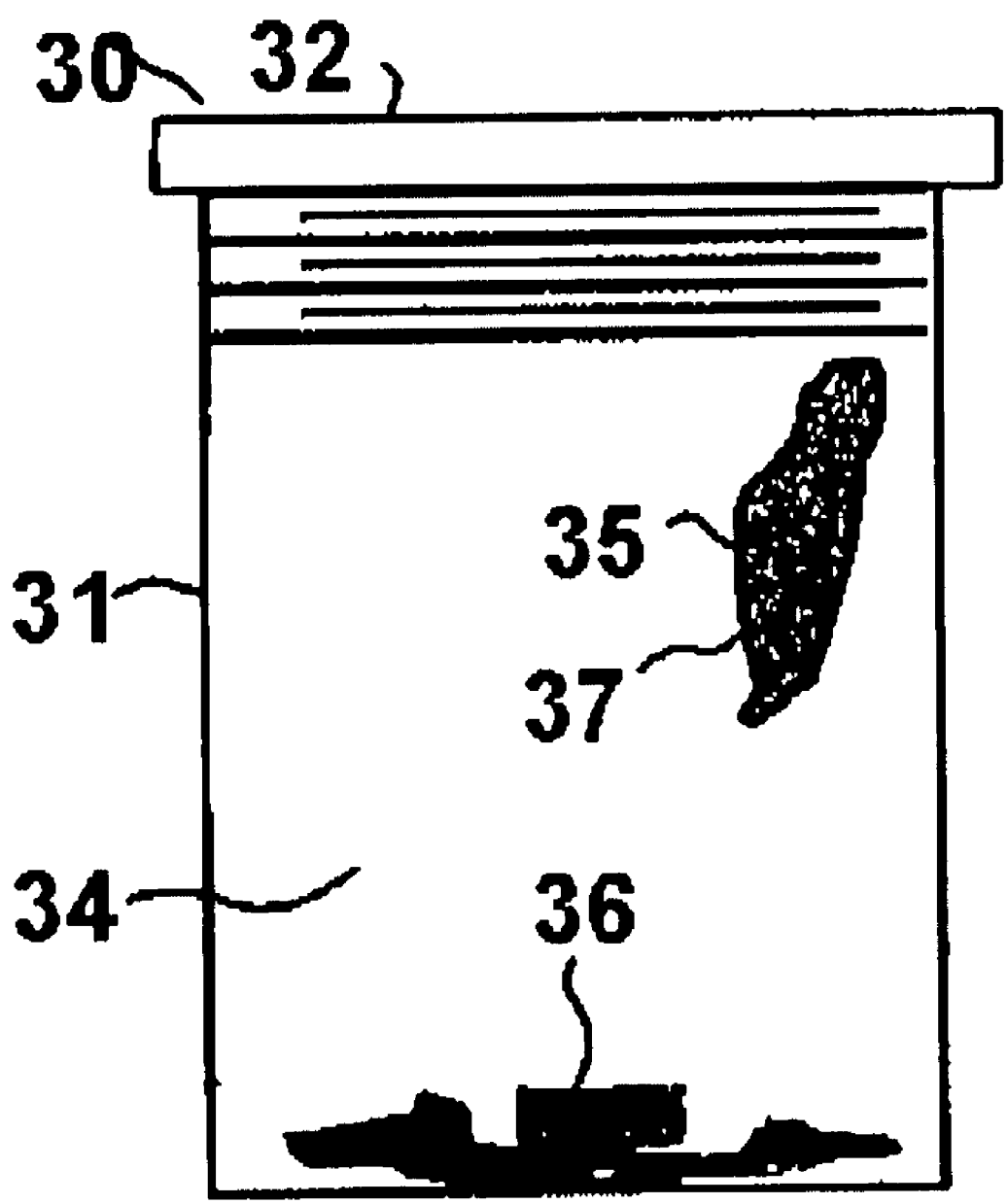
FIG. 2 is a schematic diagram of a Zero Headspace Extractor in accordance with one embodiment of this invention.

The invention claimed herein is a method and apparatus for determining release rates of contaminants from soils using sorptive resins while avoiding direct contact of the resin with the soil/NAPL complex. The apparatus comprises a low-cost Zero Headspace Extractor (ZHE) vessel 30 as shown in FIG. 2 comprising a transparent reactor vessel 31 comprising sealable means 32 for introducing at least one volatile liquid sample 34 into the transparent reactor vessel 31. Contained within transparent reactor vessel 31 is at least one sorptive resin 35. Also contained within transparent reactor vessel 31 are separation means for preventing direct contact between the at least one sorptive resin 35 and the sample 34 whereby solvent soluble constituents of the sample 34 are able to pass through the separation means to be sorbed by the at least one sorptive resin 35. In accordance with one preferred embodiment of this invention, transparent reactor vessel 31 comprises stirring means for stirring the contents thereof. It will be apparent to those skilled in the art that stirring of the contents may be achieved by a variety of means both internal and external to transparent reactor vessel 31. In accordance with one particularly preferred embodiment of this invention, said stirring means comprises a magnetic stirring system 36 contained within transparent reactor vessel 31. In accordance with another embodiment of this invention, said stirring means comprises a sonication system.

A critical element of this invention is the separation means by which the sorptive resin is maintained separate from the sample being analyzed. In addition to maintaining a separation between the sorptive resin and the sample being analyzed, one requirement of the separation means is permeability to solvent soluble constituents of the sample so as to enable sorption by the sorptive resin. In accordance with a particularly preferred embodiment, said separation means comprises at least one dialysis bag in which the sorptive resin is contained.

As previously stated, one object of this invention is to provide a zero headspace extraction device that allows sorptive resins to be used to determine release rates of contaminants from soils while avoiding direct contact of the sorptive resin with the soil/NAPL complex. The primary configuration of the zero headspace extractor device of this invention serves to accomplish this objective. The device is a low cost apparatus for contacting soil with a liquid, for maintaining a gas headspace volume equivalent to virtually zero percent of the total contents of the contact chamber, and for employing an sorptive resin for measurement of contaminant releases from the soil in the liquid phase, for example water, of the contact vessel without direct contact between the resin and the soil solids. Dialysis bags are particularly suitable for this application. Solids, including colloidal materials, are kept outside of the dialysis bag while water soluble constituents, including contaminants desorbed from the soil/NAPL complexes pass through the bag to be sorbed onto the sorptive resin. Thus, only the water soluble (or solvent soluble) volatile/semi-volatile contaminants are adsorbed onto the resin.

In addition to enabling the determination of release rates, the device of this invention is also suitable for determining the partition coefficients of volatile and semi-volatile contaminants and can be used to estimate the mass of contaminant that is rapidly released. A wide range of dilutions can be applied to the partition tests using this device. The device can be operated with up to 50 grams of soil and diluted with water for a total volume of 500 ml. The device can be used for serial dilution partitioning testing for determining rapid release fractions using soil to water ratios ranging from about 1:1 to about 260:1. Serial dilution partitioning testing is employed to determine the rapid release fractions (RRF) and the slow release fractions (SRF) of contaminated masses. The serial dilution equation derivation is based on mass balances and partitioning isotherms concepts. The serial dilution equation is as follows:

$$1/C_w = (1/X_i^{io})(L/M) + K_i^i/X_i^{io}$$

where:

$X_i^{io}$=initial concentration of available contaminants in soil, mg/kg $C_w$=concentration of contaminant in water, mg/l (24 hr)

$K_i^i$=partitioning constant of the RRF, L/Kg

L/M=water to soil mass ratio, L/Kg soil

The rapid release fraction is determined by dividing the available fraction with the initial contaminant mass.

In accordance with one preferred embodiment of this invention, the zero headspace extractor of this invention comprises a transparent reactor vessel produced from glass. Suitable sorbents for placement into the dialysis bags include sorptive resins, alumina, ion exchange resins, charcoal and mixtures thereof. Once filled, the dialysis bags are inserted into the glass reactor vessel, which is then sealed with a TEFLON-coated stopper 40, as shown in FIG. 2. When water is the solvent, most sorbent-filled dialysis bags exhibit some degree of buoyancy and are suspended in the top half of the saturated contents of the glass reactor vessel. A variety of dialysis bags with different sizes of molecular weight cut off (5,000 to 200,000) can be utilized. A septum provided at the top of the glass reactor vessel allows easy addition and removal of volatile liquid samples using syringes. These glass reactor vessels may then be agitated on a magnetic plate. When used in accordance with the methods disclosed herein, more than 90% of the volatiles initially present in the volatile liquid sample are removed from the water to the resin.

EXAMPLE 1

In this example, soil which was dominated by BTEX, polyaromatic hydrocarbons (PAHs) and total petroleum hydrocarbon (TPH) was homogenized and measured in 10 gram aliquots. A resin bag containing 3 grams of resin was prepared and inserted into transparent reactor vessels. The transparent reactor vessels were sacrificed at regular intervals. The volatiles extracted from the soils were adsorbed onto the resin and most of the volatiles and semi-volatiles were found to be removed by means of the resin through the dialysis membrane.

EXAMPLE 2

Figure 3:
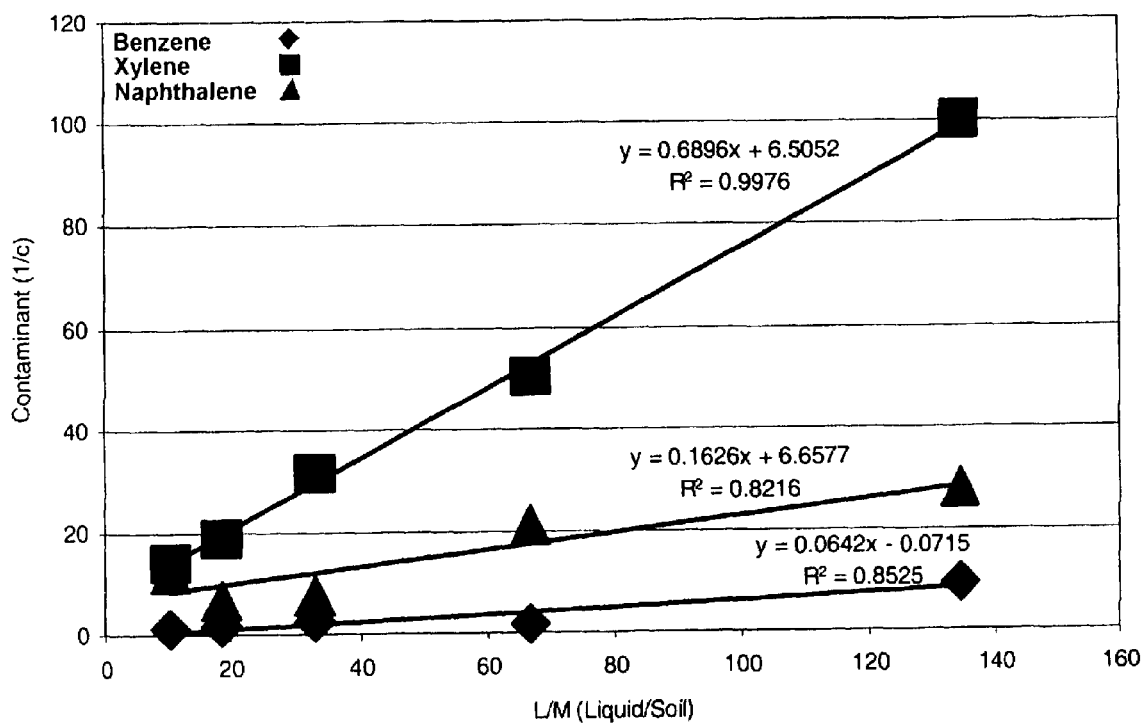
FIG. 3 is a diagram showing the partition coefficient and rapid release fraction for a sample comprising benzene, xylene and naphthalene (Sample 1)
Figure 4:
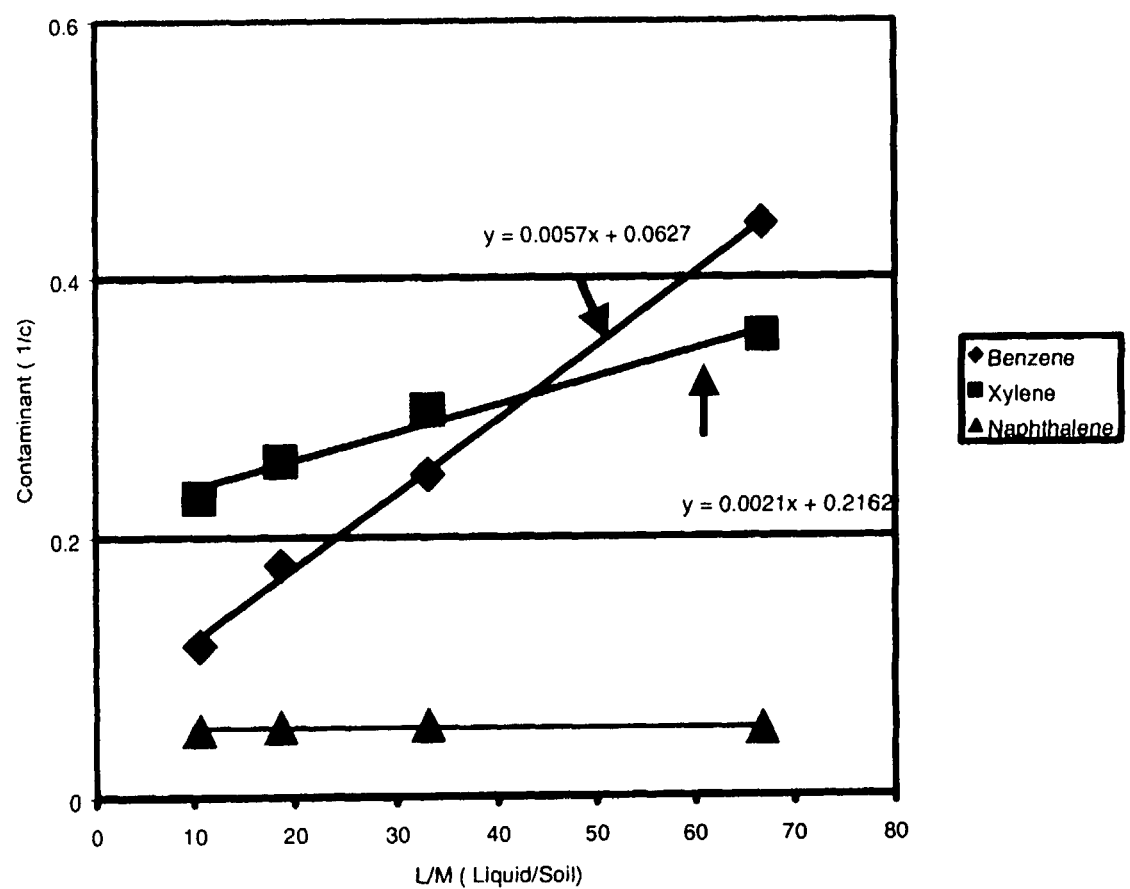
FIG. 4 is a diagram showing the partition coefficient and rapid release fraction for a sample comprising benzene, xylene and naphthalene (Sample 2)

In this example, two samples were processed for the determination of partition coefficient and rapid release fractions (benzene) in modified zero headspace units in accordance with one embodiment of this invention. These samples were tested by varying the liquid to soil ratio in the range from about 11:1 to about 134:1. The results obtained with Sample 1, shown in FIG. 3, suggest a regression coefficient of 0.85 and 0.82 respectively, for benzene and naphthalene. The results obtained for Sample 2 are shown in FIG. 4. Table 1 summarizes the results obtained for benzene, xylene and naphthalene utilizing the modified Synthetic Precipitation Leaching Procedure employing the zero headspace units in accordance with one embodiment of this invention.

TABLE 1

Summary of SPLP Data for Two Contaminant Samples

| Sample No. | Benzene | Xylene | Naphthalene |
|---|---|---|---|
| 1 | 0.886 mg/l | 0.071 mg/l | 0.008 mg/l |
| 2 | 8.61 mg/l | 4.34 mg/l | 19.5 mg/l |

The results summarized in Table 2 were obtained with samples containing only benzene and show a variation of <15% using two different methods for determining the rapid release fraction. These samples were selected due to large variation in their benzene concentrations.

TABLE 2

Comparison of Rapid Release Fractions Using Different Determination Methods

| | | Rapid Release Fraction (%) | |
|---|---|---|---|
| Sample No. | Soil Conc. (mg/kg) | Resin Test | Serial Dilution |
| 1 | 23.5 | 57.4 | 66.3 |
| 2 | 202 | 90.4 | 86.9 |

EXAMPLE 3

Figure 5:
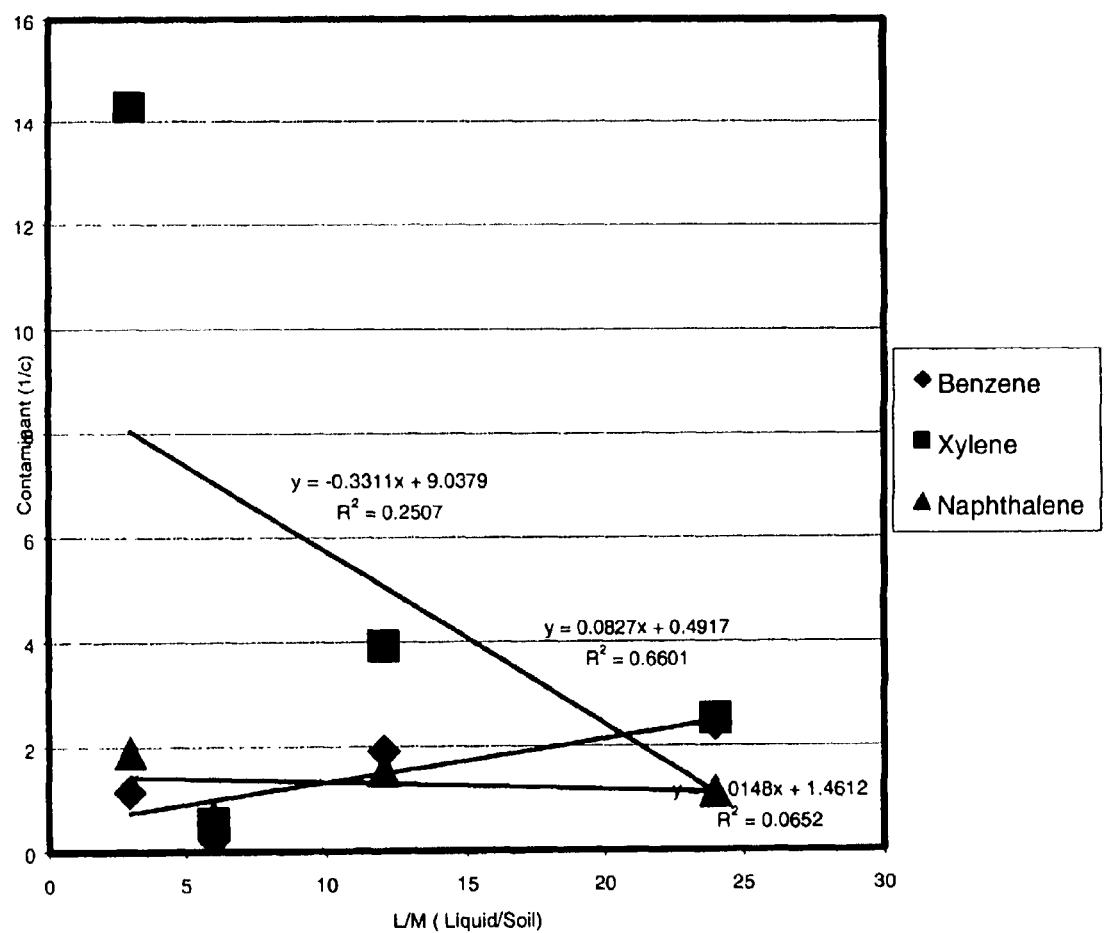
FIG. 5 is a diagram showing the partition coefficient and rapid release fraction for a sample comprising benzene, xylene and naphthalene (Sample 3) determined using a conventional ZHE unit.
Figure 6:
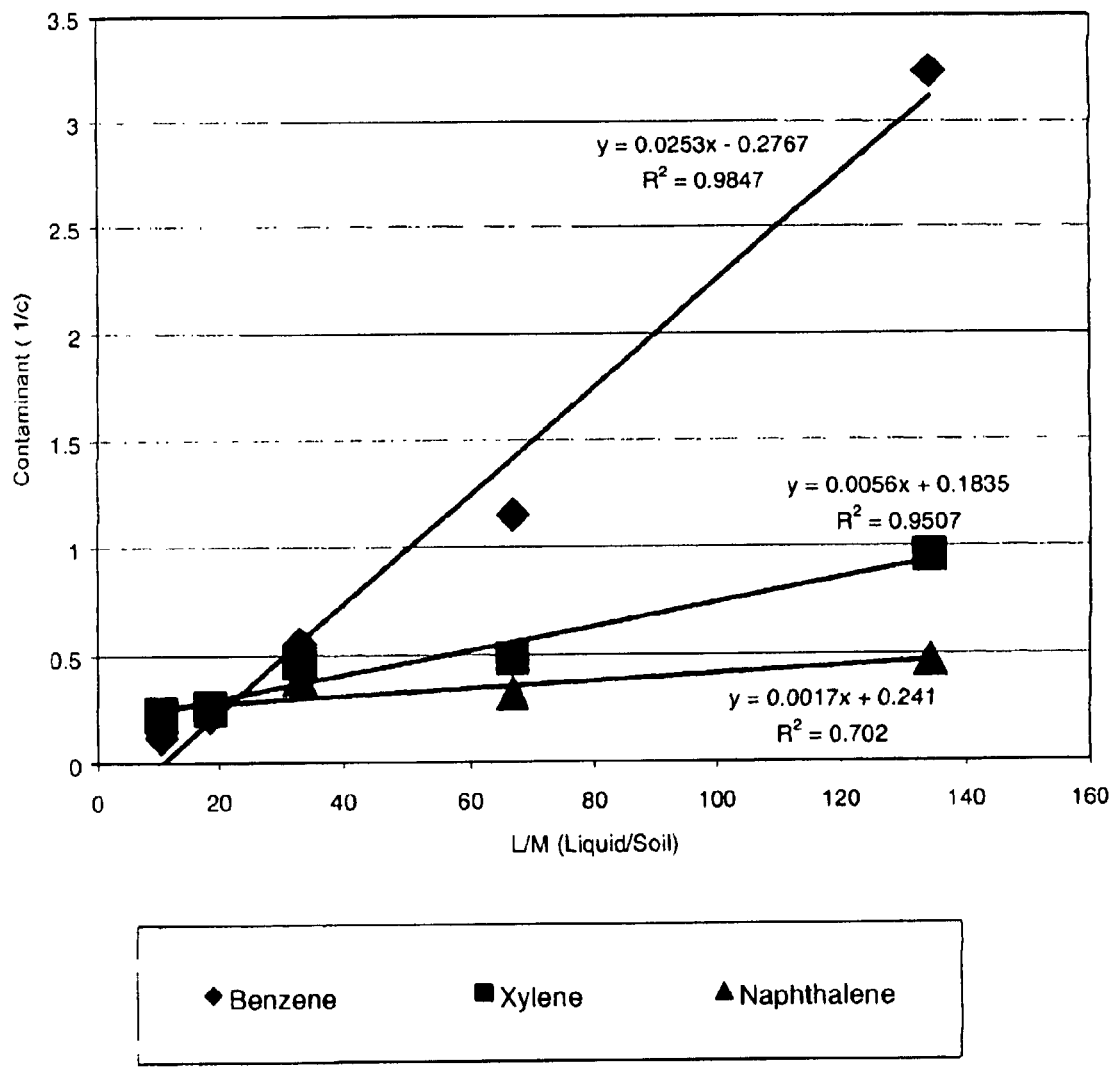
FIG. 6 is a diagram showing the partition coefficient and rapid release fraction for a sample comprising benzene, xylene and naphthalene (Sample 3) determined using a modified ZHE unit in accordance with this invention.
Figure 7:
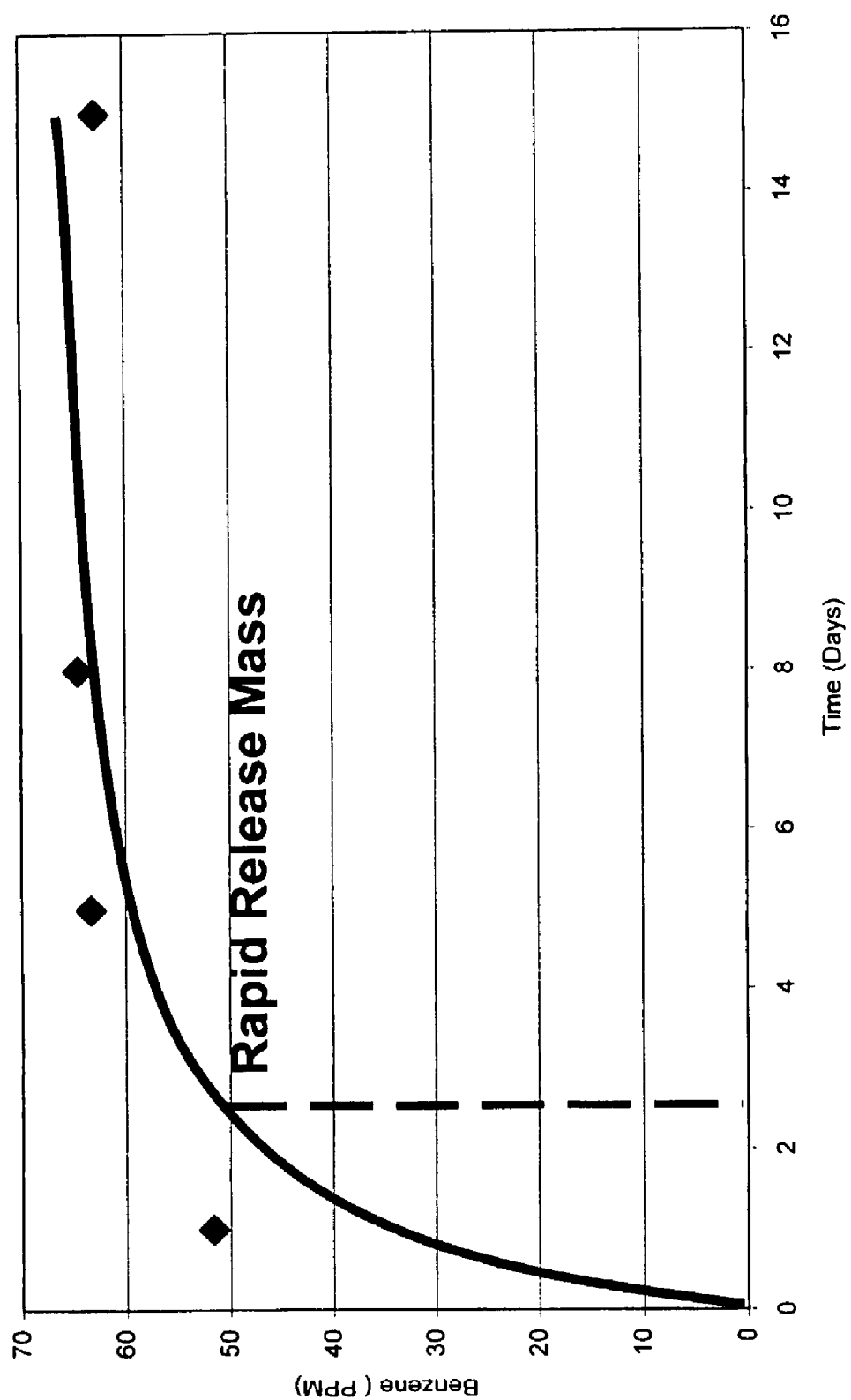
FIG. 7 is a diagram showing the rapid release fraction determination in resin test for benzene.

In this example, two samples were processed in conventional and modified zero headspace units. The results, summarized in FIG. 5, show a very poor correlation for naphthalene and benzene using conventional ZHE units. The results of processing the same samples in a modified ZHE unit in accordance with one embodiment of this invention, shown in FIG. 6, revealed a high correlation, greater than about 0.98 for benzene. The rapid release fraction from the resin test was determined by a curve fitting (FIG. 7). In addition, the rapid release fraction for benzene showed a good correlation between the resin tests and the serial dilution tests performed in modified ZHE units in accordance with this invention. In contrast thereto, the rapid release fraction determined using conventional ZHE units was relatively low, as shown in Table 3.

TABLE 3

Comparison of Rapid Release Fraction
for Conventional and Modified ZHE Units

| | | Rapid Release Fraction (%) | | |
| --- | --- | --- | --- | --- |
| | | Conventional | Modified ZHE Units | |
| Samples | Soil Conc. (mg/kg) | ZHE Unit | Resin Test | Serial Dilution |
| 3 | 64.7 | 18.9 | 77.3 | 61.1 |
| 4 | 15.4 | 13.3 | 69.7 | 89.2 |

These examples demonstrate that the modified ZHE unit in accordance with this invention is very effective in determining the rapid release fraction of volatile compounds such as benzene. Independent experiments performed on set of samples demonstrate a good reproducibility with standard deviation within 20% variations between different samples processed. Thus, the modified ZHE units in accordance with this invention are very suitable for mixing of samples using magnetic stirrers.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. A method for measuring release rates of contaminants in at least one of a fast mode and a slow release mode comprising the steps of:

introducing at least one volatile liquid sample into a transparent reactor vessel comprising sealable means for introducing said at least one volatile liquid sample into said transparent reactor vessel and sealing said at least one volatile liquid sample in said transparent reactor vessel, at least one sorbent contained within said transparent reactor vessel, and a separation means for maintaining a separation between said at least one sorbent and said at least one volatile liquid sample in said transparent reactor vessel, whereby substantially zero headspace is maintained within said transparent reactor vessel;

passing at least one solvent soluble constituent present in said at least one volatile liquid sample through said separation means, resulting in sorption of said at least one solvent soluble constituent by said at least one sorbent;

removing said at least one solvent soluble constituent from said at least one sorbent through said separation means; and measuring the amount of said at least one soluble constituent removed from said at least one sorbent, and then determining the release rates of contaminants comprising of said at least one solvent soluble constituent in at least one of a fast release mode and a slow release mode.

2. A method in accordance with claim 1, wherein said at least one volatile liquid sample has a solids to solvent ratio in a range of about 260:1 to about 1:1.

3. A method in accordance with claim 1, wherein said at least one volatile liquid sample is mixed by at least one of magnetic stirring, mechanical agitation and sonication.

4. A method in accordance with claim 1, wherein said separation means comprises at least one dialysis bag.

5. A method in accordance with claim 1, wherein said at least one volatile liquid sample is introduced into said transparent reactor vessel without opening said transparent reactor vessel.

6. A method in accordance with claim 1, wherein said at least one solvent soluble constituent is removed from said sorbent without opening said transparent reactor vessel.

7. A method in accordance with claim 4, wherein said at least one dialysis bag has a molecular weight cutoff in a range of about 5000 to about 200,000.

* * * * *